(12) United States Patent
Carroll, III (10) Patent No.: US 6,622,401 B2
(45) Date of Patent: Sep. 23, 2003

(54) MODIFIED OXFORD SHOE PROVIDING VERTICAL AND HORIZONTAL HEEL PRESSURE DIMINISHMENT INCLUDING AN OPTIONAL MEANS OF ADJUSTING PRONATION

(76) Inventor: Lester Erwin Carroll, III, Box 762, Gulf Breeze, FL (US) 32562

( * ) Notice: Subject to any disclaimer, the term of this patent is extended or adjusted under 35 U.S.C. 154(b) by 0 days.

(21) Appl. No.: 10/198,577

(22) Filed: Jul. 18, 2002

(65) Prior Publication Data

US 2003/0014884 A1 Jan. 23, 2003

Related U.S. Application Data (60) Provisional application No. 60/306,230, filed on Jul. 18, 2001.

(51) Int. Cl.[7] ............................ A43B 21/00; A43B 13/18
(52) U.S. Cl. .............................. 36/105; 36/28; 36/35 R; 36/69; 36/142
(58) Field of Search ............................ 36/27, 28, 34 R, 36/35 R, 37, 38, 69, 105, 72 R, 72 B, 73, 142, 143, 144

(56) References Cited

U.S. PATENT DOCUMENTS

| 220,200 | A | * | 9/1879 | Whittier | 36/73 |
|---|---|---|---|---|---|
| 3,192,651 | A | * | 7/1965 | Smith | 36/105 |
| 4,187,620 | A | * | 2/1980 | Selner | 36/28 |
| 4,322,893 | A | * | 4/1982 | Halvorsen | 36/43 |
| 4,622,764 | A | * | 11/1986 | Boulier | 36/68 |
| 4,942,677 | A | * | 7/1990 | Flemming et al. | 36/27 |
| 5,042,175 | A | * | 8/1991 | Ronen et al. | 36/28 |
| 5,090,140 | A | * | 2/1992 | Sessa | 36/138 |
| 5,649,374 | A | * | 7/1997 | Chou | 36/27 |
| 5,651,196 | A | * | 7/1997 | Hsieh | 36/27 |

FOREIGN PATENT DOCUMENTS

DE           3935714        *  5/1990

* cited by examiner

Primary Examiner—M. D. Patterson (57) ABSTRACT

The modified oxford shoe providing vertical and horizontal heel pressure diminishment including an optional means of adjusting pronation is an inventive device which diminishes pressures to the heel with a floating collar and supple counter assembly with adjusting strap, with spacing studs attached strategically to the sides of the midsole to prevent exterior pressure to the heel and with a multi functioning cushion assembly coupled with adjustable underlying steel springs and resilient midsole and wearing surface to diminish pressure to the bottom of the heel and provide pronation adjustment if needed.

1 Claim, 11 Drawing Sheets

MODIFIED OXFORD SHOE PROVIDING VERTICAL AND HORIZONTAL HEEL PRESSURE DIMINISHMENT INCLUDING AN OPTIONAL MEANS OF ADJUSTING PRONATION

This application claims the benefit of Provisional application no. 60/306,230, filed Jul. 18, 2001.

BACKGROUND OF THE INVENTION

The American Podiatric Medical Association published a statistical document in 2001 relating that 18,035,600 U.S. residents over 18 were treated by physicians for heel pain in 2000, with another 20,619,200 self treated in the same year.

The present invention relates to a modified oxford shoe designed specifically for use by those experiencing chronic or acute foot pain. Precisely for therapeutic relief for those experiencing heel pain, sometimes disabling, which can occur in the back, sides and bottom of the heel with other symptoms of inflammation, redness, swelling and heat. Practitioners in the field recognize that pressures on the heel can cause pain to an otherwise uninjured heel, and that pressures on an injured heel tend to aggravate the inflammation while recovering thus extending the healing time.

Secondarily, the modified oxford shoe provides a means of correcting biomechanical imbalance such as excessive pronation which may cause chronic heel pain and may also contribute to injury to the knee, hip and lower back.

The primary purpose of shoes is to protect the foot from injury. The sole protects the bottom of the foot and the upper protects the body of the foot. Shoe designers, through their ingenuity and tenacity, have developed excellent concepts and designs for protective sports shoes. Some of these, the padded tongue, the padded collar and resilient midsole have trickled down to the walking shoe which virtually every man, woman, and child wear for work, school or leisure—because they are comfortable.

There are occasions, however, that the comfort of these shoes is not sufficient for those incurring heel pain through injuries, heel spurs, malformations or mild to severe obesity which prompts the subject invention.

The function of a conventional counter, capped by a collar, is to hold the foot into the body of the shoe and to cover the heel of the wearer. The counter of an oxford shoe, the basic design of a walking shoe, is a stiffened piece of leather, cotton or synthetic material around and attached to the heel of a shoe, formed upward and forward to follow the contour of the wearers heel creating a small encapsulated pocket which does not allow sufficient upward or downward movement of the rear of the wearers heel within the shoe to allow for a satisfactory range of internal cushioning because of friction leading to blisters. Therefore the widely sold resilient plastic heel inserts are thin and flimsy resulting in a minuscule level of cushioning, and when compressed present the same unyielding face as the underlying mass.

To attain more cushioning, it is not unusual for the buyers of the inserts to double up on these cushions in the hope of better cushioning. This lead to thicker more expensive resilient plastic inserts which have two disadvantages beyond the limited range of cushioning, especially when the wearer is experiencing severe heel pain. These inserts are flat across the beam and taper forward and downward to a point one half inch or so from the front, whereupon they abruptly taper to zero to meet the plane of the insole liner. When weight from the bottom of the heel compresses the insert, the heel forms a cup shaped depression in the top surface of the insert causing stretching of the surface resulting in a stiffening of the surface and resultant inward pressure to the heel by the sides of the depression, however slight. The weight placed by the heel upon the insert does not in any means fully compress the insert and in effect the insert then presents a non-resilient surface to the heel. The remaining height of the insert, regardless of the two tapers, raises the plane of the heel above the plane of the pad of the foot forward of the heel, therefore does not allow proper load sharing of the whole foot causing callousing to occur in the forward part of the foot with resulting additional discomfort to the foot.

Another problem that one with heel pain would encounter with a conventional fixed counter is the patients heel would in fact encounter the counter with any sideward motion of the foot creating pressure resulting in a higher degree of pain.

The corrective devices for adjusting pronation are hard plastic inserts supporting the foot from the heel through the ball. These devices are contoured as the foot should be, not as it is, resulting in substantial discomfort to the wearer. The inserts are supplied with directions acknowledging this fact and advising using these for an hour a day as a start of a progressive program to make the transition to everyday wear. Some of these devices are thicker custom designed, poorly padded and more expensive than those sold to the mass market with generic designs. The buyers of these devices generally try and discard them because of the continuing discomfort.

Utilizing steel springs as heel cushioning devices has been enduring art for many years. Early versions placed the springs in a heel under the sole of a shoe or boot which merely provided cushioning action for a healthy heel from the ground up to the sole of the shoe with hard barriers; sole, insole and leather heel liner as a platform for the wearer's heel. These methods are disclosed in U.S. Pat. Nos.: 384,634 1888 Martin; 1,094,211 1914 Jenoi 1,099,180 1914 Karacsonyi; 1,098,241 1914 Forray; 1,338,817 1920 De Luca; 2,535,102 1950 Taylor; and 2,669,038 1954 De Werth. Later with the advent of sports shoes the focus turned to shock absorption, stability and energy return through spring related devices as shown in U.S. Pat. Nos.: 5,544,431 1966 Dixon; 5,649,374 1997 Chou; 5,651,196 1997 Hsieh; 5,729,916 1998 Vorobiev; 5,743,028 1998 Lombardino; 5,832,629, 1998 Wen; 6,006,449 1999 Orlowski; and 6,055,747 2000 Lombardino.

While the concepts and designs of these devices or shoes may be effective for their intended uses, they all contain cushioning obstructions, barriers and impedences which negate their performance when attempting to eliminate pressure, or reduce the sense of impression caused by compression to an injured heel.

Specifically, this representative group has disclosed no suitable, by design or implication, direct adjustable cushioning extending unimpededly from the patients heel to the floor for this purpose.

Properly designed and manufactured oxford shoes are available in various lengths and widths to provide a comfortable supportive fit. There is no provision for inserts which change the working dimensions of the shoe. This demands the most cautious discretion in making internal changes to a shoe unless other compensating adjustments are made to the shoe.

There are those practitioners who feel that the platform for the pad of a foot should not be flat as generally manufactured. Since the heel pad is lower in its static state than the adjoining foot pad, they reason that the platform of a shoe should have a depression in the heel to conform with this. The fact that this may be controversial and difficult to engineer appears to be the basis for the flat platform existing in most shoes.

BRIEF SUMMARY OF THE INVENTION

The objects of the present invention are: To provide a shoe which immediately delivers vertical and horizontal heel pressure diminishment for those experiencing acute or chronic heel pain;

To provide a series of heel cushioning, with no intervening barriers or other impedences, extending from the patients heel to the floor;

To provide a vertical heel pad cushioning series independent of any lateral or lengthwise forces upon which the patients heel directly rests, and exerts downward pressure upon to receive buoyantly elastic cushioning;

To provide a cushioning element which spreads the downward pressure from the patients heel over a larger area of buoyantly elastic cushioning springs;

To provide a variety of calibrated compression springs of various cushioning resistance for selection by the patient determined by the patients weight and degree of buoyantly elastic cushioning desired;

To provide ease of access to the calibrated springs for periodic patient changing;

To provide a secondary cushioning series, wherein the first element of cushioning, compresses additionally to bridge the transition from buoyantly elastic to resiliently elastic cushioning when the calibrated springs are depressed to a limit determined by the depth of the resilient floor of the upper midsole cavity. On this occasion the bottom of the lower portion of the cushion assembly rests upon this resilient floor, and additionally spreads the downward pressure. Simultaneously, the elastic periphery of the upper and lower midsole cavities is compressed by the resilient flexible face of the wearing surface providing a cushioning effect against the lower faces of the calibrated springs. At no point are the springs fully compressed;

To provide the patient the ability to tilt the cushion assembly, if needed, to adjust the interface with the patients heel;

To provide a floating collar and supple upper counter assembly with adjusting strap whereby the upper counter is not attached to the heel of the shoe and the movement of the assembly is generally controlled by the padded collar preventing internal pressures to the heel or heel stem. The adjusting strap ends can be partially or fully released to allow a longer range of motion to accommodate sideward motion of the heels;

To provide strategically placed removable spacing studs for the midsole to eliminate exterior pressure to the patients heel while driving;

To provide a therapeutic shoe in attractive contemporary designs with several finishes for prolonged use.

Other objects and advantages of the present invention will become obvious to the reader and it is intended that these objects and advantages are within the scope of the present invention.

In this invention the vertical and horizontal heel pressure diminishment for those experiencing chronic or acute heel pain is achieved with a number of both internal and external modifications to a shoe of oxford design.

A floating collar and supple counter assembly with adjusting strap eliminates side and rear interior pressure to the patients heel by virtue of the collar assembly not being fixedly attached to the heel of the shoe. The collar assemblies pivot points at the upper waist of the shoe, the suppleness of the counter and the straps adjustment function allow the collar assemblies upward, downward, left and right movement to occur with no internal pressure to the heel.

A series of removable spacing studs mounted strategically onto the vertical sides of the shoes midsole which eliminate external pressure to the heel when the shoe is on edge while driving. At this stage the floating collar assembly will shift to the downside eliminating internal pressure from the patients heel to the counter. The floating collar assembly will then cradle the rear of the foot. The spacing studs will provide clearance between the counter and the floor of the vehicle which eliminates any external pressure to the heel.

A bidirectional unimpeded series of adjustable cushioning to the bottom of the heel, extending directly from the patients heel to the floor.

The elements of this cushioning series includes from the top 1) A laminated cushion assembly with the upper portion formed of resilient gel type plastic with an initial elliptical oblique terrace which conforms to the shape and direction of the patients heel, followed by other oblique terraces, and portions thereof, which sequentially increase in area until reaching the lower portion, which is formed of flexible plastic with twelve positioning studs, which rests upon 2) Twelve calibrated, changeable by patient, steel springs in three files which extend through 3) An upper midsole cavity in the resilient midsole sized to accommodate the cushion assembly under pressure from the patients heel. 4) Twelve lower midsole spring holding cavities, wherein the springs rest upon the wearing surface of the shoe attached to the midsole. 5) The exterior face of the wearing surface bordered by the chamfers fore and aft of the heel.

The following will further explain the mechanics of the direct unimpeded series of adjustable cushioning for the bottom of the heel.

For one with intense heel pain, the aggregate cushion value of the twelve calibrated springs per shoe should start at twenty five percent of the clothed body weight for the initial fitting.

The patient, with both shoes on, should stand upright with the feet comfortably apart, which spreads the body weight to the pads of both feet.

The conformation of the patients body then will determine the portion of full body weight directed to the heels. This can be determined by the patient rocking gently forward and backward. The patient should be able to feel the cushion assembly rise going forward and depress going backward.

At this point this is what has happened: with the patient standing, pressure from the patient's heels depressed the top oblique cushioning terrace of the cushion assembly into the second oblique cushioning terrace with no cupping or stretching back pressure; the lower part of the cushion assembly spread and shared the downward pressure with the upper faces of the twelve calibrated springs beneath, which then compressed into the upper midsole cavity giving buoyantly elastic cushioning to the heel; the supple counters of the floating collar and supple counter assembly with adjusting strap flex downwardly under the downward motion, resulting in no irritating movement of the collar or counter against the heel or heel stems; additional indirect downward pressure from the foot structures, adjacently forward of the cushion assembly, is exerted through the midsole to the flexible resilient outer faces of the shoes wearing surfaces, causing pressure which slightly compresses the lower faces of the twelve calibrated springs and the lower face of the lower midsole cavities providing a measure of additional cushioning. All of this occurs in milliseconds.

As the patient rocks forward: The collars of the floating collar and counter assemblies with adjusting straps, under slight upward pressure from the heel stem rise causing the supple counters, along with the adjusting straps, to unflex and rise slightly from the midsole; this places no pressure on the heel or heel stem; the downward pressure from the heels ceases, allowing both the elliptical terraces and the springs to regain their static condition, as do the flexible faces of the wearing surfaces.

When the patient rocks backward the above standing sequences repeat. Then the extra pressure from more weight exerted upon the heels causes: The calibrated springs to compress further allowing the lower portion of the cushion assembly to rest upon the floor of the upper midsole cavity; the patients heels further compress the oblique cushioning terraces; pressure is exerted upon the floor of the resilient upper midsole by the cushion assembly; pressure is exerted upon the flexible resilient outer face of the shoes heel wearing surface causing sandwich pressure upon the floor of the upper midsole cavity and the bottom plane of the lower midsole spring cavities along with both ends of the calibrated springs which produces resilient elastic cushioning.

The action of standing, rocking forward and rocking rearward, as described, demonstrates the dynamics of the elements of the bidirectional unimpeded series of adjustable cushioning.

The cushion assembly under downward pressure from the patients heel hovers within the upper midsole cavity over its floor, as described. In this position, the heel is on plane with the rest of the foot pad which eliminates the prevailing problem of improper weight loading to the forward pads of the foot by conventional heel inserts.

In this hovering state only a portion of the oblique elliptical terraces are compressed thus retaining resiliency while sharing the load with the resilient springs beneath. There is no cupping or full compression of the oblique elliptical terraces occurring in the area contacted by the patients heel.

When a step is taken and the lead heel contacts the floor at the point of the rear midsole chamfer, pressure is exerted simultaneously upon the lower face of the wearing surface and the cushion assembly initiating cushioning. As the face of the heel wearing surface becomes horizontal, the primary force is downward from the patients heel to the top oblique ellipse. With some terraces compressing the load is spread from the patient's heel area over the larger area of the cushion assembly reducing effective pressure to the patients heel as the load is shared with the twelve springs. The springs may compress on plane with the floor of the upper midsole cavity, at which time the remaining terraces of the cushion assembly resiliently compress instantly sharing the load with the floor of the upper midsole cavity. As the foot rolls forward the pressure to the patients heel is reduced to zero.

This sequence does not occur with conventional heel inserts nor any of the prior art relating to spring cushioning of the heel.

The springs are the only variable element of the bidirectional unimpeded series of adjustable cushioning found in this invention. The initial strength of the springs is determined by a percentage of the clothed weight of the patient and then adjusted by the patient, who best knows, for the patients level of comfort. For this reason the springs are readily accessible for changing by lifting the cushion assembly.

The skeletal integrity of the human body relies substantially upon the stability of its platform, the feet. Practioners in the field have relied on inserts to correct insufficiencies in this area. These, as described, are contoured as the foot should be, which is too much treatment too fast in addition to defeating proper sizing of a shoe.

The platform presented to a patients heel in the present invention rests on and is controlled by the underlying springs. The positions of the springs and the clearances provided by the cushion assembly lends itself to tilting with springs of varying strengths properly placed to provide a sequential training force to receive correction without discomfort.

DETAILED DESCRIPTION OF THE INVENTION

Figure 1:
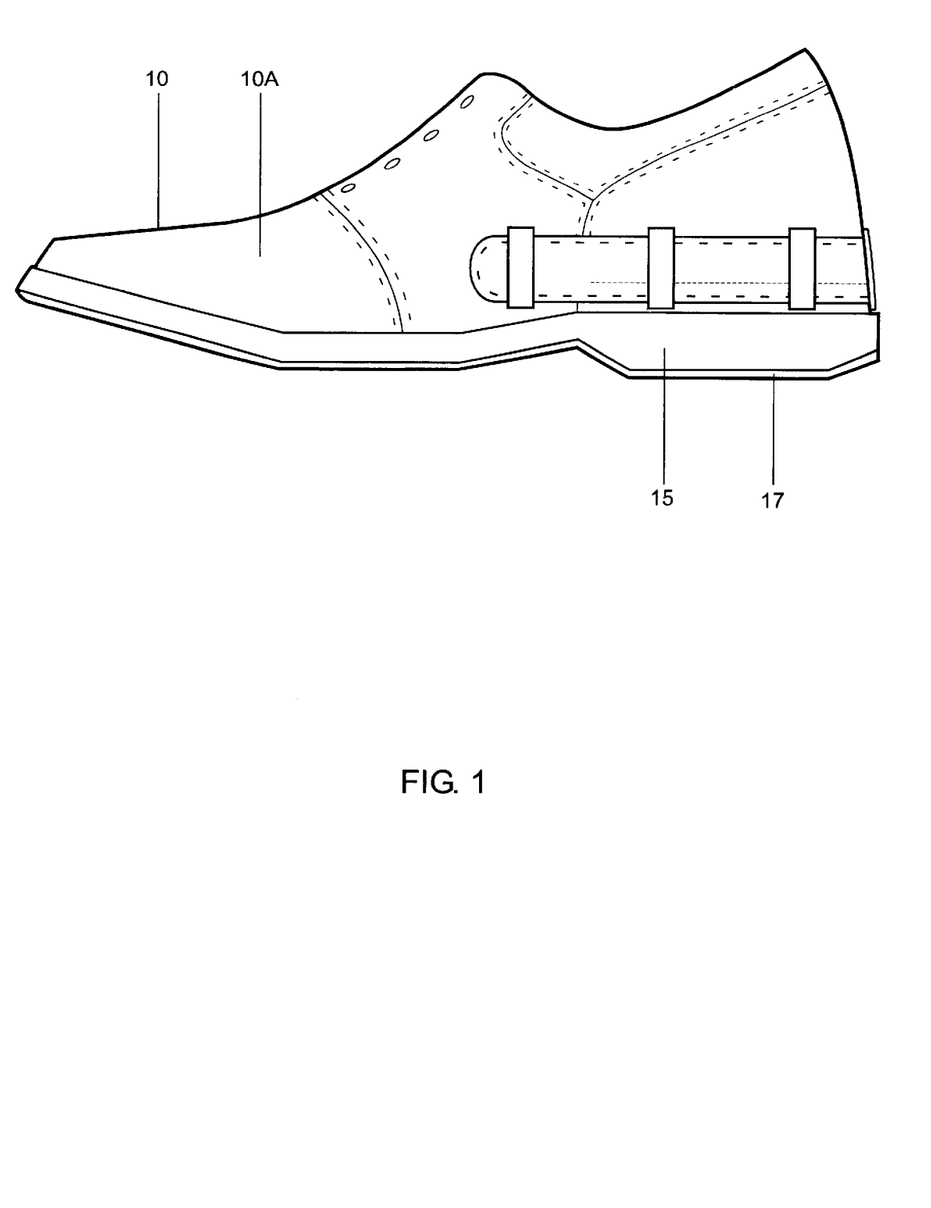
FIG. 1. is a side view of a shoe in accordance with the present invention.

FIG. 1 (10) illustrates a preferred embodiment of a shoe of modified oxford design. It is constructed with a thin rubber or synthetic wearing surface (17), a midsole (15) of resilient foamed polyurethane type material for cushioning and an upper (10A) of leather, cotton or synthetic material. The lower fixed counter FIG. 2(14) being of stiffened leather, cotton or synthetic material and the upper floating counter FIG. 2(12) being of supple leather, cotton or synthetic material. The collar FIG. 2(11) is padded as shown in FIG. 3(11A) FIG. 6(11A) FIG. 6A(11A) whereby the padding extends inward.

Figure 1A:
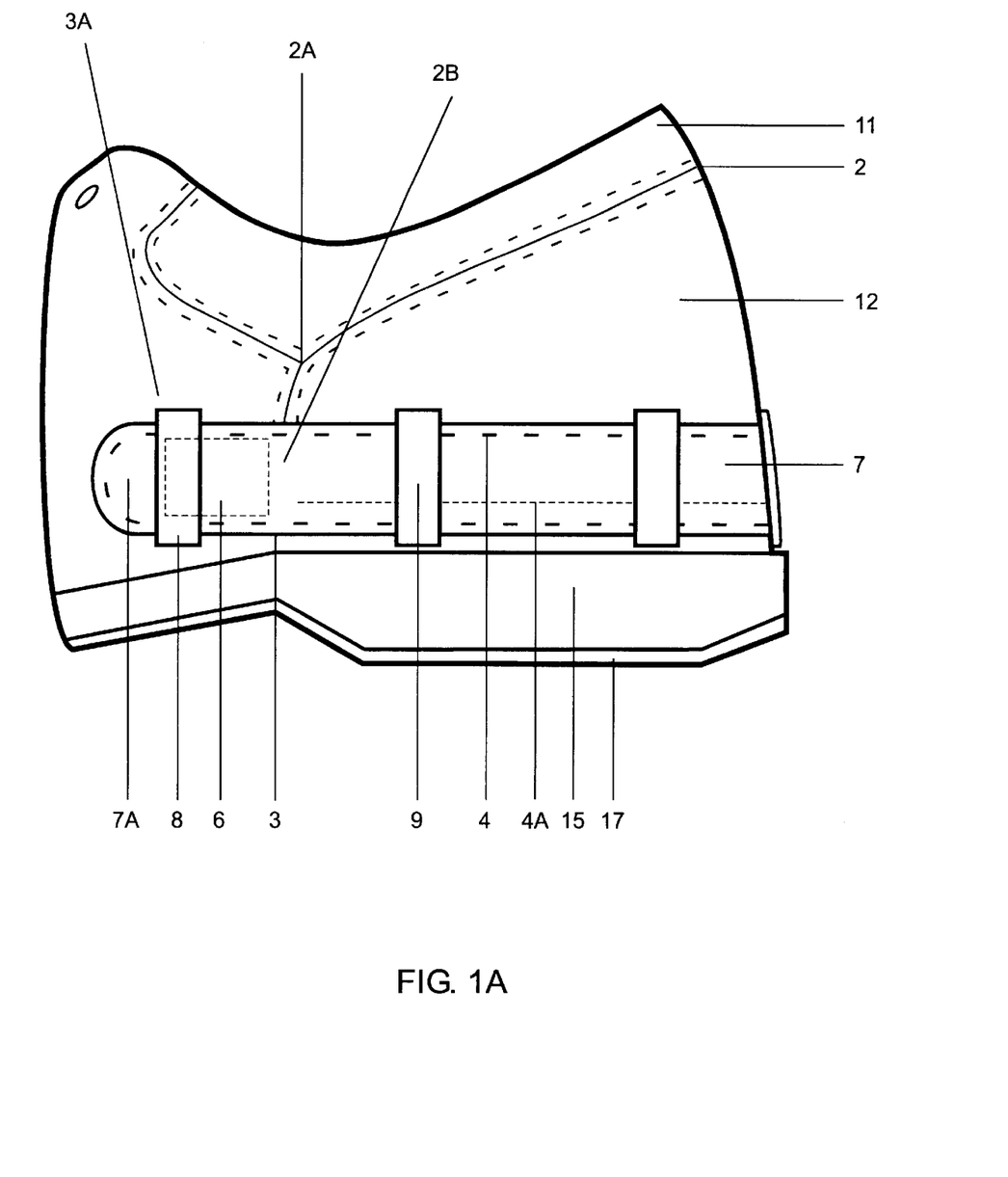
FIG. 1A. is a partial side view of a shoe illustrating components of the floating collar and supple counter assembly with adjusting strap in accordance with the present invention.
Figure 6:
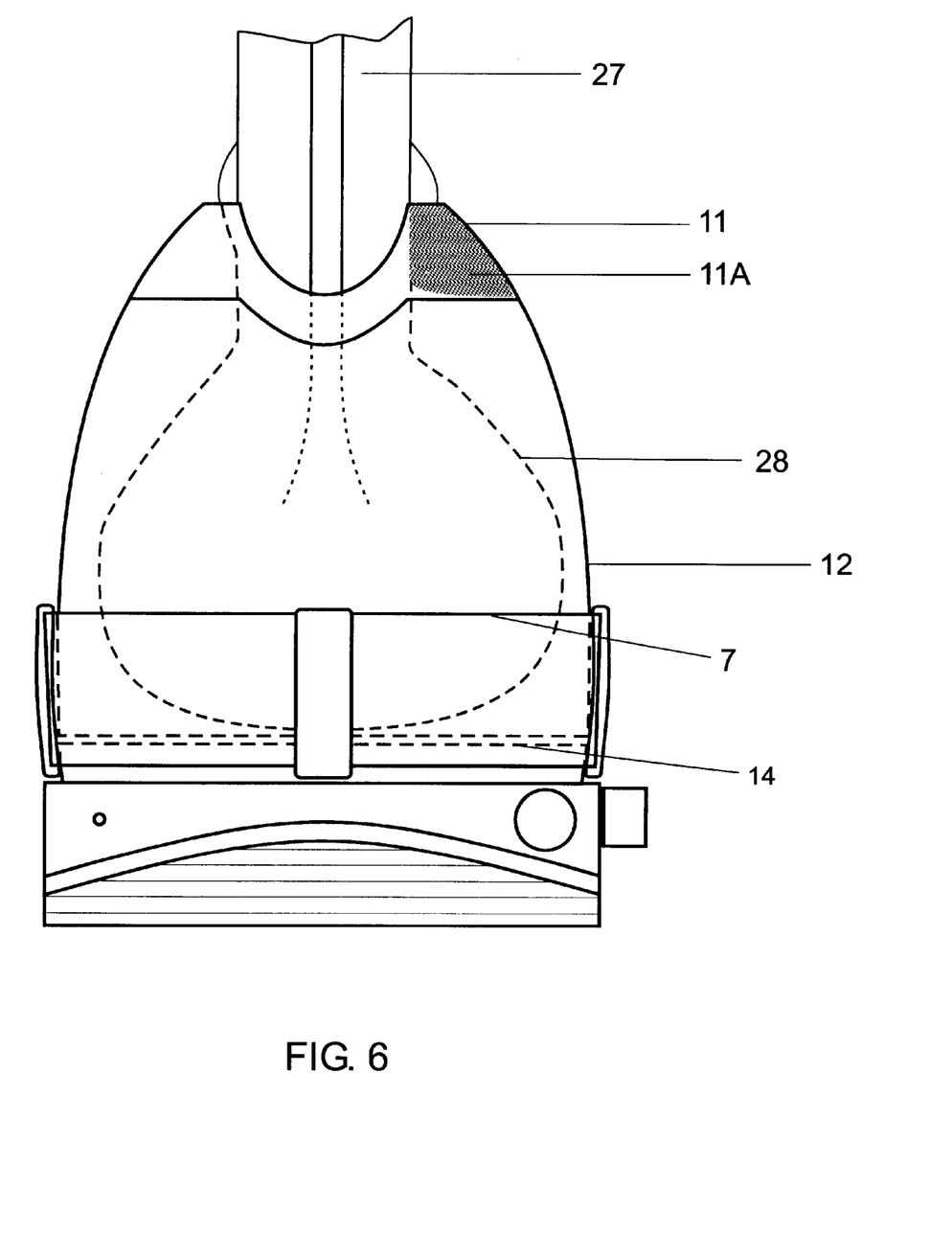
FIG. 6. is a rear view of a shoe illustrating the components of the floating collar and supple counter assembly with adjusting strap and other related data in accordance with the present invention.
Figure 6A:
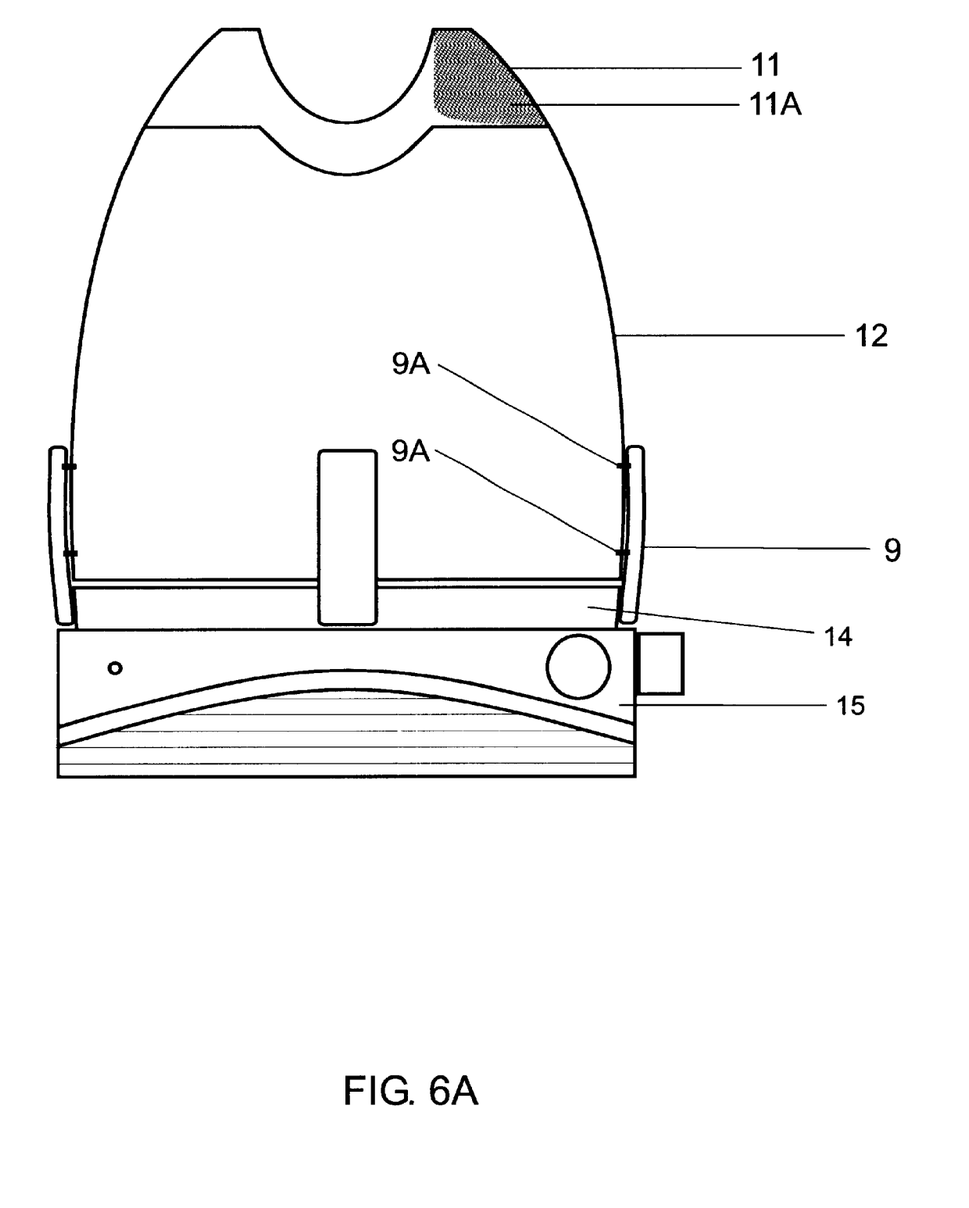
FIG. 6A. is a rear view of a shoe, partially cutaway, illustrating the padding of the collar, its relative attachment to the supple counter, the attachment of the floating strap loops to the supple counter and other related data in accordance with the present invention.

FIG. 1A shows the adjusting strap (7) of the collar and supple counter assembly with adjusting strap, FIG. 1A(11, 12,7) which extends around the rear of the shoe and terminates at a point equal to that shown on the reverse side. All of the adjusting strap loops FIG. 1A(9) located aft of the juncture of the backpart and the waist FIG. 1A(3) are attached to the floating supple upper counter FIG. 1A(12) as shown in FIG. 6A(9) (9A). The space between the loop and the counter is for illustration only. The bottom of the loops FIG. 6A(9) extend adjacently to the top surface of the midsole FIG. 6A(15) allowing the adjusting strap FIG. 6(7) to cover both the lower portion of the floating supple counter FIG. 6(12) and a major portion of the fixed lower counter FIG. 6(14).

The segment of the adjusting strap FIG. 1A(7) also aft of the juncture of the backpart and the waist FIG. 1A(3) is attached to the floating, supple counter FIG. 1A(12) by the stitching FIG. 1A(4)(4A).

Figure 2:
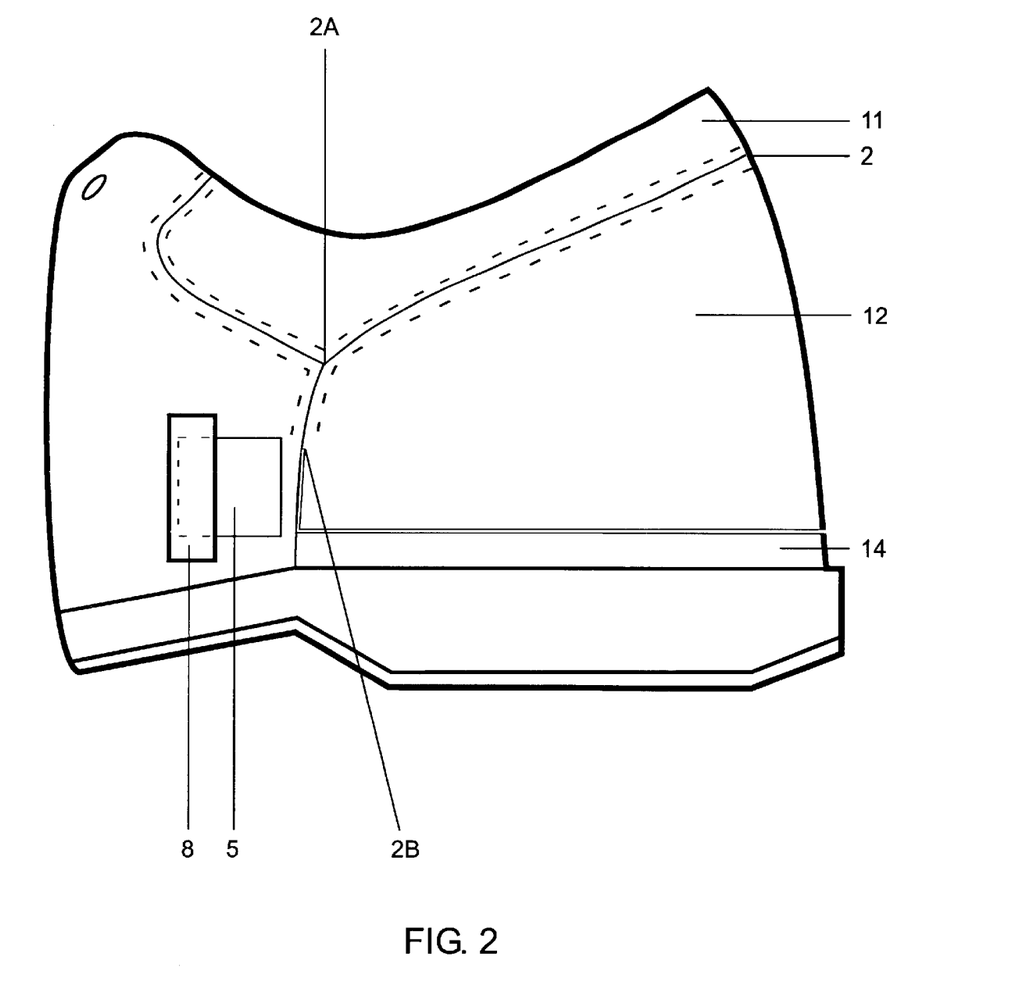
FIG. 2. is a partial side cutaway view of a shoe illustrating components of the floating collar and supple counter assembly with adjusting strap in accordance with the present invention.
Figure 3:
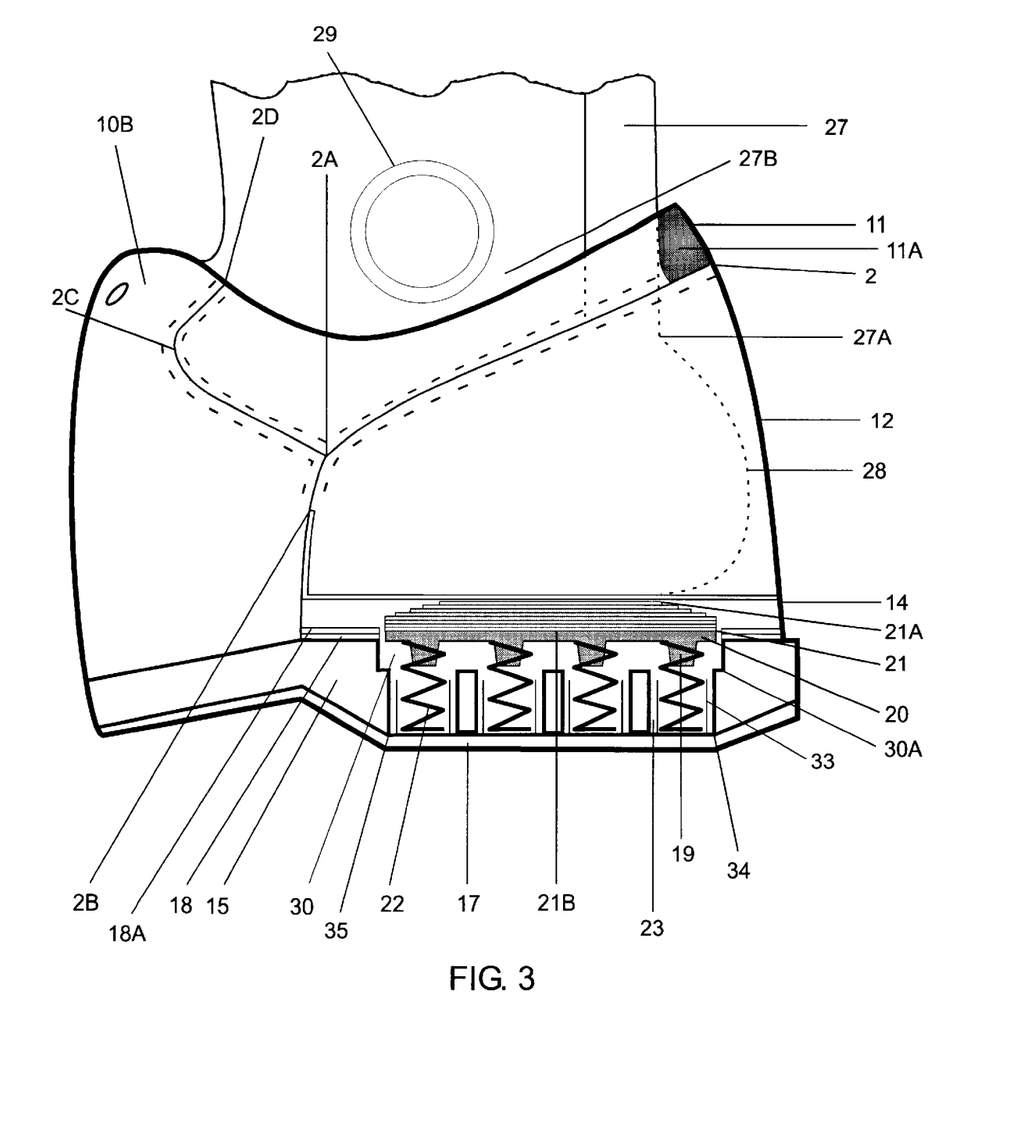
FIG. 3. is a partial side cutaway view of a shoe illustrating components of the floating collar and supple counter assembly and components of the bidirectional unimpeded series of adjustable cushioning in accordance with the present invention.

The adjusting strap loops FIG. 1A(8) forward of the juncture of the backpart and the waist FIG. 1A(3) are attached to the waist of the shoe FIG. 1A(3A) as shown in FIG. 2(8) to house the unsecured ends FIG. 1A(7A) of the adjusting strap FIG. 1A(7). Forward of the juncture of the backpart and the waist FIG. 1A(3) the broken line box FIG. 1A(6) signifies hook Velcro attached to the reverse side of the unattached ends FIG. 1A(7A) of the adjusting strap FIG. 1A(7) forward of the juncture of the backpart and the waist FIG. 1A(3). This fastens adjustably, with the clinging pile velcro shown in a line and broken line box in FIG. 2(5). The unattached ends FIG. 1A(7A) of the adjusting strap FIG. 1A(7) when pulled forward and pressed firmly to couple the hook Velcro FIG. 1A(6) with the clinging pile Velcro FIG. 2(5) cause the lower part of the floating supple counter FIG. 6(12) to align with the lower fixed collar FIG. 6(14).

In this static state the padded floating collar FIG. 3(11A) makes contact with the rear of the stem of the heel FIG. 3(27) which prevents pressureable contact of the rear of the bulb of the heel FIG. 3(28) with the floating supple upper counter FIG. 3(12). FIG. 6(27) shows the sides of the heel stem making contact with the padded floating collar FIG. 6(11A) and somewhat forward and below the ankle FIG. 3(29), the side of the foot FIG. 3(27B) making contact with the padded floating collar FIG. 3(11A). FIG. 6(28) shows that the sides of the heel bulb are prevented from pressureable contact with the floating flexible upper counter FIG. 6(12).

The placement of the lower edge of the floating padded collar FIG. 3(11) commences at a point FIG. 3(2), above and to the rear of the juncture of the heel bulb and heel stem FIG. 3 (27A) and extends forward to the rear edge of the waist of the shoe FIG. 3(2A) whereupon it is attached to the waist, then to its juncture FIG. 3(2C) with the lacing vamp FIG. 3(10B) whereupon it is attached upwardly to the lacing vamp to the point FIG. 3(2D).

This placement of the floating padded collar FIG. 3(11) positions it above the heel bulb FIG. 3(28) and below the ankle FIG. 3(29) whereby it controls the movement of the collar assembly. This control function of the floating padded collar will neither place pressure upon the heel bulb nor interfere with movement of the ankle.

To accomplish the space between the sides FIG. 6(28) and rear FIG. 3(28) of the heel bulb and the floating supple upper counter FIG. 6(12) FIG. 3(12) the floating supple upper counter FIG. 2(12) is attached to the outside lower edge of the padded floating collar FIG. 2(11) commencing at the point FIG. 2(2) where it extends forward to the rear edge of the upper waist FIG. 2(2A) then it is attached to the rear lower waist to a point FIG. 2(2B) behind the adjusting strap FIG. 1A(7). This places the padded surface of the floating padded collar FIG. 6A (11A) FIG. 3(11A) inboard of the floating supple upper counter thus maintaining aforementioned space. The collar padding conformation is shown in FIG. 6(11A) FIG. 6A(11A) FIG. 3(11A). The floating supple upper counter is further attached to the adjusting strap FIG. 1A(7) by decorative stitching FIG. 1A(4,4A). This allows the adjusting strap, when loosened to react to movement along with the supple upper counter. When standing or walking the floating padded collar and resilient counter assembly with adjusting strap FIG. 1A(11)(12)(7) eliminates any side or rear pressureable contacts to the sides of the heel.

When sitting or reclining the feet tend to move subconsciously. For this reason the free ends of the adjusting strap FIG. 1A(7A) can be loosened partially or entirely to free the upper counter FIG. 1A(12) and its adjusting strap FIG. 1A(7) to its free floating state whereby no pressure is sensed, either to the right or left.

Figure 7:
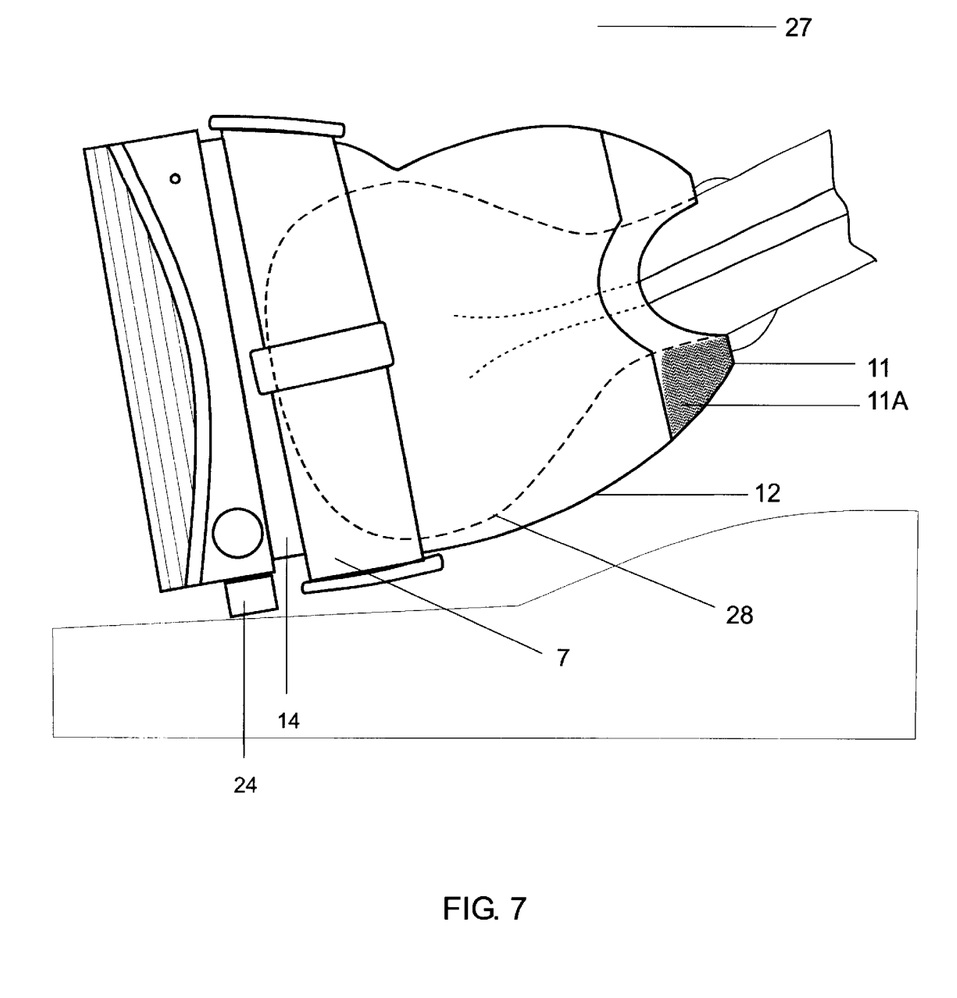
FIG. 7. is rear view of a shoe illustrating an alternative position of the floating collar and supple counter assembly with adjusting strap and other related data in accordance with the present invention.

When driving a car, SUV or the like it is usual for drivers, generally men, to place the accelerator controlling foot on the right edge of the heel of the shoe and at an angle to the accelerator pedal. In a conventional shoe with a fixed rigid counter, all of the weight of the driver's leg is transferred to the side of his heel which is then pressed into the fixed wall of the counter creating substantial pressure upon the wearer's heel. When the free ends FIG. 1A(7A) are disengaged the floating padded collar and resilient counter assembly with adjusting strap can freely move to the right creating a soft cradling effect eliminating pressure to the heel bulb FIG. 7(28) as shown in FIG. 7(11)(12)(7). The patients heel can also slide to the right and partially over the lower fixed collar FIG. 7(14) as there would be little or no downward pressure exerted upon the cushioning mechanism, so the top of the obliquely terraced cushion FIG. 3(21A) would be on or about the plane with the lower fixed counter FIG. 3(14) presenting no impedance. The removable spacing studs FIG. 4(24)(25), FIG. 7(24) attached to the right rear and rear of the midsole portion of the right shoe (left rear and rear of the midsole portion of the left shoe when necessary) provide clearance from the floor to avoid contact with the floating padded collar and resilient counter assembly in it's released state FIG. 7(11)(12)(7). For those, generally women, who experience this pressure on the rear of their heel, an additional removable stud FIG. 4(25A) may be placed on the left rear of the midsole into the receptacle (right rear of left shoes midsole when necessary) for the same result.

As will be explained, the bidirectional series of unimpeded adjustable cushioning consists of reciprocating downward and upward motion of the patients heel upon the cushion assembly within the inward portion of the back part of the shoe as part of the method of pressure relief to the patients heel. A conventional fixed collar and counter in a situation such as this would cause friction to bear on the wearers heel resulting in injury including blisters to the heel of the wearer. The floating padded collar and supple counter assembly with adjusting strap eliminates this friction by rising with the foot, due to the controlling action of the padded collar and its unattached state upon upward motion and depressing due to the suppleness of the floating counter upon downward motion.

The following description of the mechanics of the bidirectional uninterrupted unimpeded series of adjustable cushioning will explain its cushioning function and therapeutic value upon the bottom of the patients heel which directly bears weight of various intensities.

Figure 4:
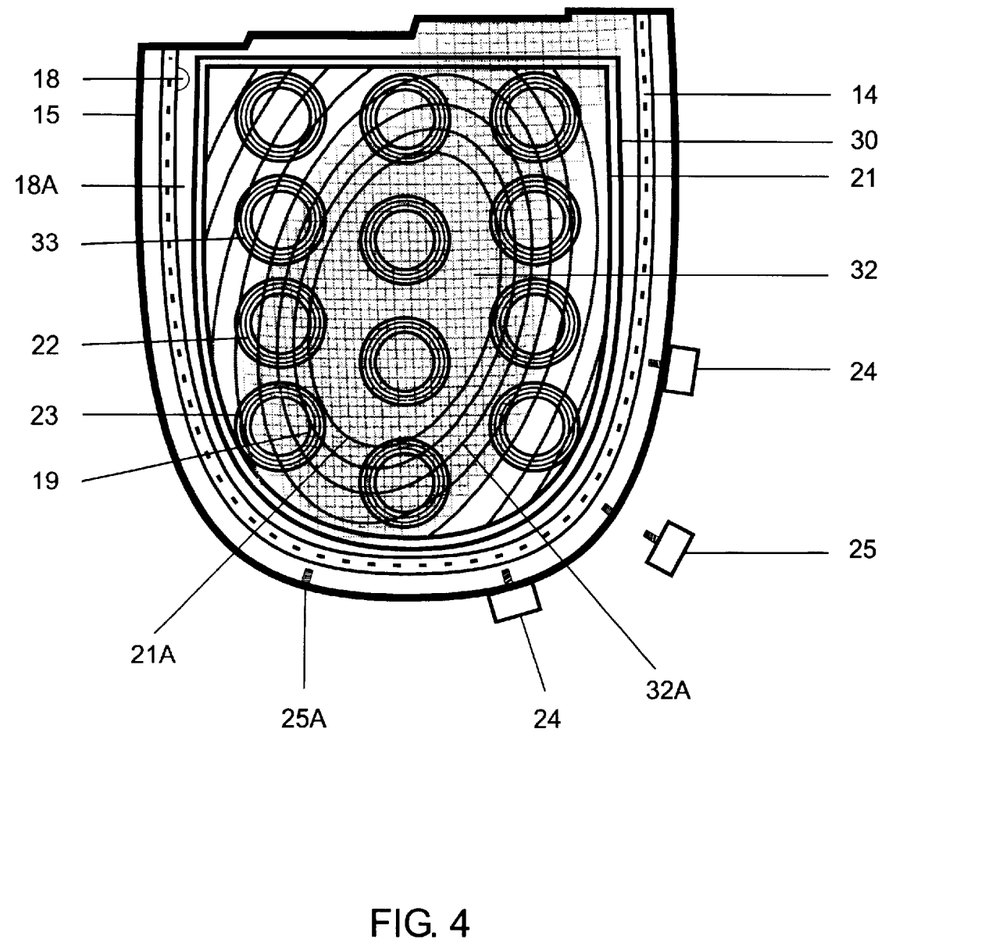
FIG. 4. is a top partially cutaway view of the heel of a shoe illustrating placement of cushioning components of the bidirectional unimpeded series of adjustable cushioning and other parts in accordance with the present invention.
Figure 5:
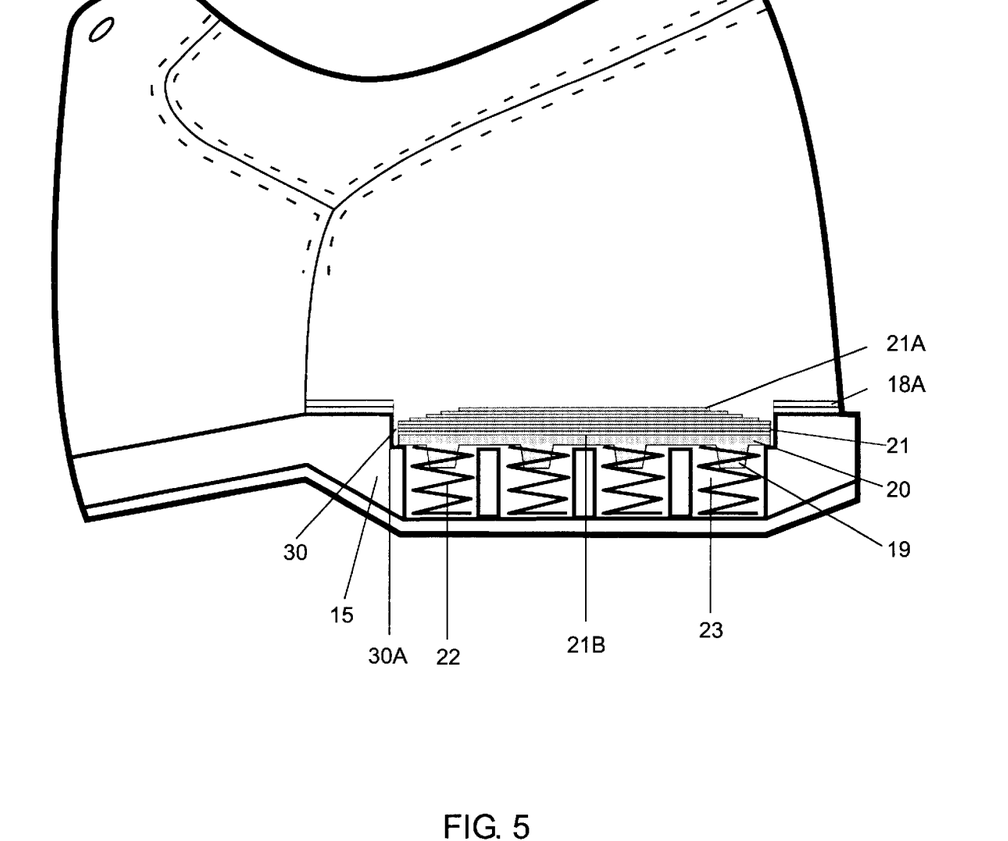
FIG. 5. is a partial side cutaway view of a shoe illustrating more mechanics of the bidirectional unimpeded series of adjustable cushioning in accordance with the present invention.

The first element of the bidirectional cushioning is the cushion assembly FIG. 3(19)(20)(21), FIG. 4(21), FIG. 5(19)(20)(21) which is a multi functional devise of laminated plastic which is an indicator of the measure of essential attention to detail required as it relates to the field of pressure relief, in this instance, to injured heels.

The accompanying art will show the patients right heel pad and the forwardly continuing foot pad are oblique to the centerline of the heel cavity FIG. 4(32), (screened area), and housed as such in the heel cavities of conventional shoes and the instant invention. The angle of this placement is due to the shape of a normal foot FIG. 8(40).

The upper portion FIG. 3(21), FIG. 4(21), FIG. 5(21) of the cushion assembly is formed of resilient gel type plastic with an elliptical terrace FIG. 4(21A) at the top of the cushion. This terrace conforms to the shape of and obliqueness of the patients heel. Each successive, generally concentric terrace or partial terrace area sequentially increases until reaching the laminate line FIG. 3(21B), FIG. 5(21B).

Conventional heel cushioning inserts present a face to the patients heel extending from the periphery of the inner heel cavity of a shoe. The mass of cushioning material that the patients heel does not contact is unnecessary and causes unneeded transversal and longitudinal resistance which impedes the cushioning value of the insert.

This elliptical oblique pyramidal design provides initially a cushioning terrace somewhat smaller than the surface of the patient's heel pad. Upon downward force from the patient's heel the top terrace compresses into the next larger terrace with no cupping nor inward pressure.

This sequence could continue until the upper portion of the cushion assembly becomes compressed to the extent of the force exerted upon this elliptical oblique pyramidal cushion when resting on a non resilient barrier as do conventional heel inserts.

Not so in the instant invention as will become apparent.

The lower portion FIG. 3(20), FIG. 5(20) of the cushion assembly is formed of flexible plastic from the point of lamination to the upper part, with twelve blunt cone shaped positioning studs FIG. 3(19), FIG. 4(19),(inner ring) FIG. 5(19) protruding from its lower face, which are concentric with the twelve lower spring cavities FIG. 3(23),FIG. 4(23) (outer ring), FIG. 5(23) of the midsole FIG. 3(15), FIG. 4(15), FIG. 5(15). The studs are sized at their inception to enter, with clearance, the top of the voids of the twelve calibrated compression springs FIG. 3(22), FIG. 4(22) (second inner ring), FIG. 5(22) which are housed partially within the twelve lower cavities FIG. 3(23) FIG. 4(23) (outer ring) FIG. 5(23) of the midsole thereby creating a cushioned seat for the cushion assembly FIG. 3(19)(20)(21), FIG. 4(21), FIG. 5(19)(20)(21). The top of the cushion assembly FIG. 3(21A), when no downward pressure being exerted upon it is on plane with the top of the lower fixed counter FIG. 3(14). The perimeter of the cushion assembly FIG. 4(21) is congruent with the perimeter of the resilient walls of the upper midsole cavity FIG. 4(30). There is adequate clearance between the cushion assembly and the walls of the upper midsole cavity for the cushion assembly to be depressed into the upper midsole cavity either perpendicularly or slantingly.

Another function of the cushion assembly is to spread the downward pressure from the area of the patients heel FIG. 4(32) (screened area) to the larger area of the faces of the twelve calibrated cushioning springs it rests upon FIG. 4(22).

Figure 4A:
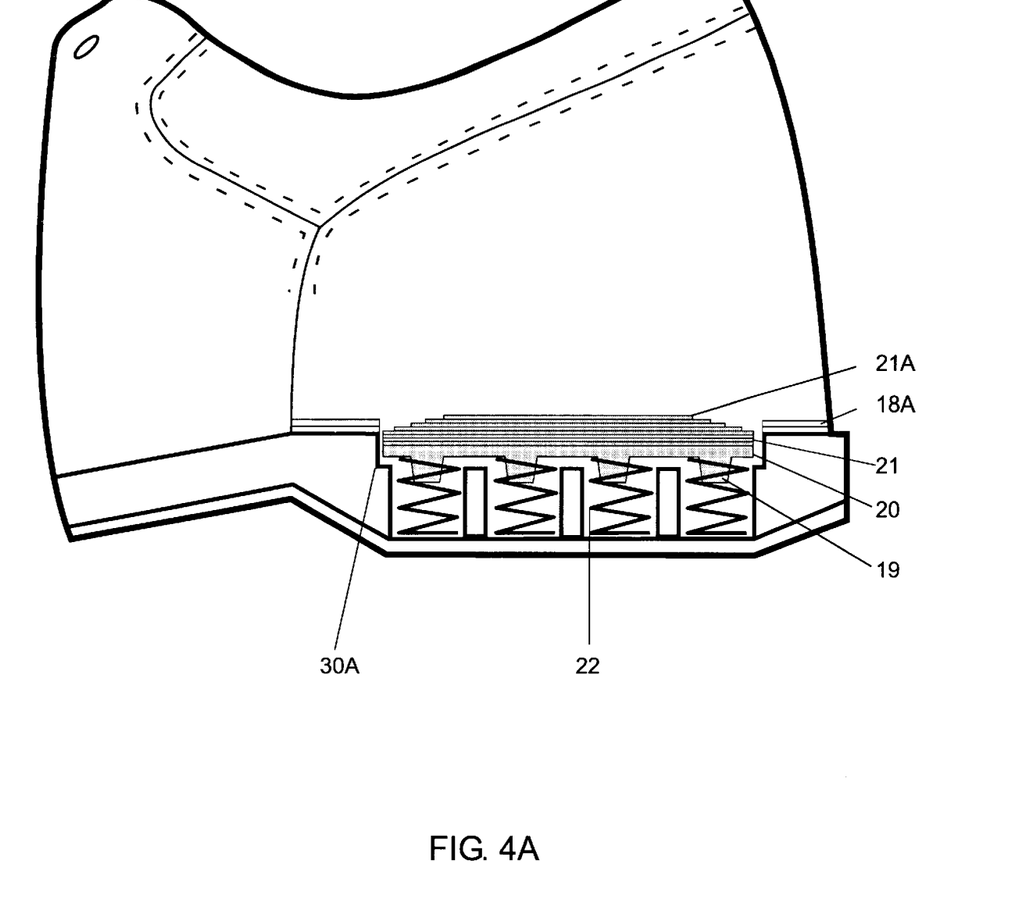
FIG. 4A. is a partial side cutaway view of a shoe illustrating mechanics of the bidirectional unimpeded series of adjustable cushioning in accordance with the present invention.

Inasmuch as the aforementioned upper portion FIG. 4A(21)is an integral part of the cushion assembly FIG. 4A(19,20,21) it follows that the downward force from the patients heel FIG. 4(32) upon the elliptical oblique terraces FIG. 4(32A) would be shared with the properly calibrated twelve springs FIG. 4A(22) FIG. 4(22) (second inner ring) supporting the cushion assembly resulting in a hovering state over the floor of the upper midsole cavity FIG. 4A(30A). This buoyantly elastic cushioning state is achieved with neither the cushioning terraces nor the cushioning springs reaching their full cushioning capacities.

In this hovering state the top of the cushion assembly FIG. 4A(21A) is generally on plane with the insole liner FIG. 4A(18A)providing the flat surface found in conventional shoes.

Figure 8:
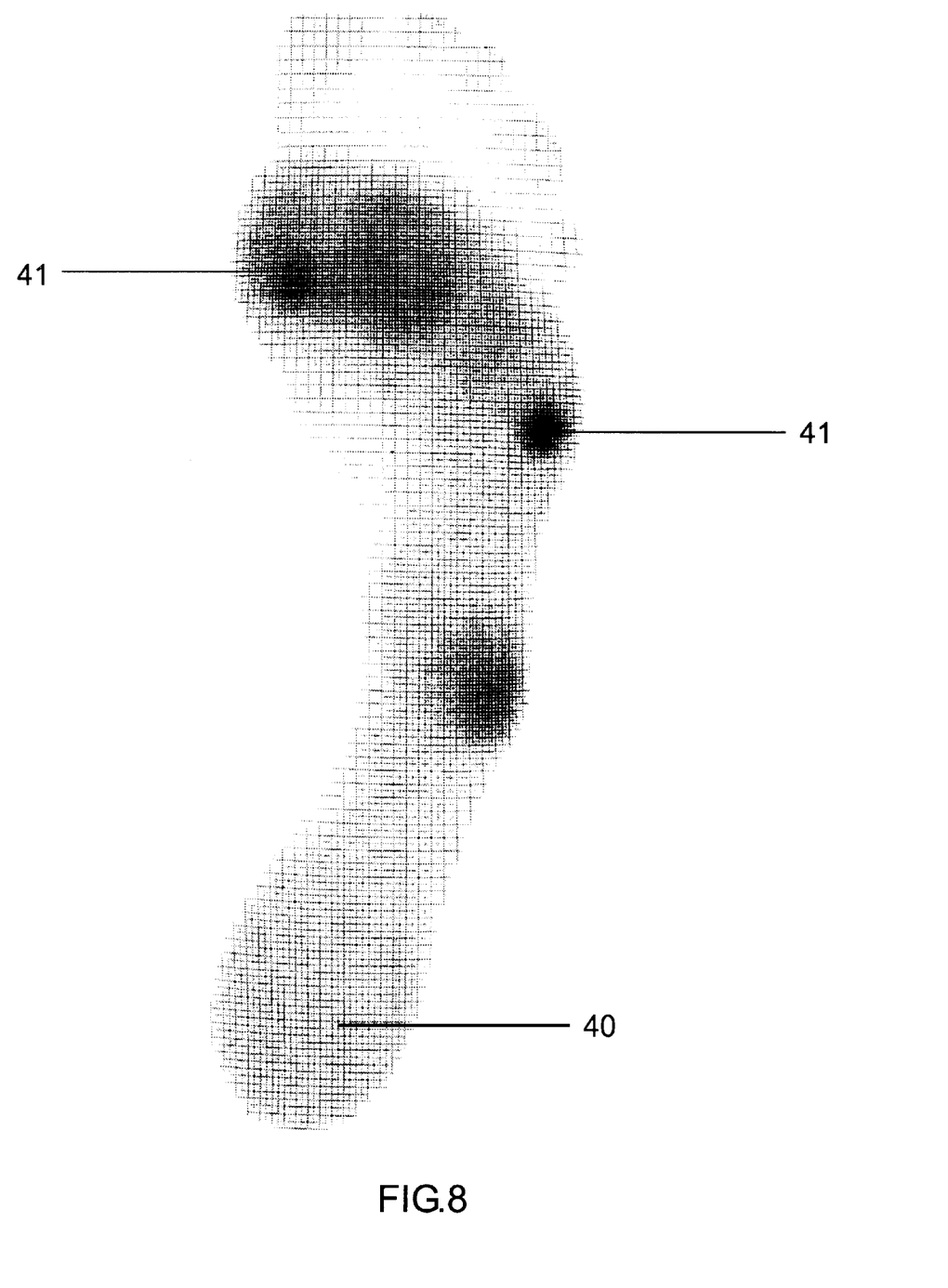
FIG. 8. is a right foot print calibrated for pressure in a walking state on a hard surface of a patient with acute heel pain which relates to the present invention.

As described, conventional heel inserts, even when compressed add height to the internal heel area of a shoe causing pressure to the front parts of the foot resulting in moderate to severe callouses and shown by the darkened areas FIG. 8(41).

FIG. 5(30A) shows the cushion assembly resting on the floor of the supper midsole cavity with the top of the cushion assembly FIG. 5(21A) being somewhat below the plane of the insole liner FIG. 5(18A). The range between the above, hovering cushioning state and the following, resiliently elastic cushioning state is desirable in keeping with paragraph 0014.

On the occasions when the cushion assembly compresses the top faces of the springs FIG. 5(22) flushly with the floor of the upper midsole cavity FIG. 5(30A) the cushion assembly FIG. 5(19,20,21)further spreads the load from the patient's heel to the resilient cushioning floor of the upper midsole cavity whereby the patient's heel is cushioned continuously by both buoyantly elastic and resiliently elastic means with no barriers or other impedances to the ground.

Please refer to paragraphs 0032–0039 which the following will more fully explain.

In the initial selection of calibrated springs, while standing, it is desirable to have the balance of cushioning shared between the oblique elliptical cushioning terraces of the cushion assembly FIG. 4A(19, 20, 21) and the calibrated springs FIG. 4A(22) whereby the cushion assembly hovers slightly over the floor of the upper midsole cavity FIG. 4A(30A) providing the patient with buoyant elastic cushioning with the least amount of resistance.

For one with extreme heel pain it is best for the patients well being to take short, slow, flat, steps which spreads the weight over all of the foot pads and maintains the buoyant elastic cushioning for most comfort.

As the pain abates the length and pace of the flat steps can be increased which should maintain the state of buoyant elastic cushioning.

As the patient recovers further full, regular, slow, strides may be taken. With the initial soft springs in place and the edge of the rear chamferred heel of the shoe making first contact with the floor the following sequence occurs. The patient's heel places pressure on the cushion assemblies top few oblique cushioning elliptical terraces which cushionly compress sharing the load with the calibrated springs which in turn cushionly compress until the top faces of the springs reach the floor of the upper midsole cavity FIG. 5(30A) at which time the cushion assembly FIG. 5(19,20,21) spreads the load to the catacombic resilient midsole floor. Then the remaining, subject to the patient's weight and speed of the pace, oblique, elliptical, cushioning terraces compress resulting in a brief imperceptical shift into resilient elastic buoyancy.

As the patient picks up the pace more pressure is exerted which brings the flexible resilient face of the wearing surface FIG. 3(34) to (35) into cushioning play. This is discussed in paragraph 0021.

The patient may elect to increase the calibrated spring strength at this point or earlier during recovering as a personal preference, to prolong the periods of buoyantly elastic cushioning.

These spring changes are easily accomplished by lifting the cushion assembly, taking the springs out and replacing them within the floating spring cavity liners.

The backpart of the midsole FIG. 1A(15), FIG. 4(15) extending to the rear from the waist FIG. 1A(3) to the end of the shoe and the portion of the flexible wearing surface FIG. 1A(17) attached thereto provides: a base for the lower fixed counter FIG. 2(14), FIG. 4(14); housing for the depressed cushion assembly FIG. 5(30); housing for the calibrated springs FIG. 3 (23), FIG. 4(23) (outer ring) FIG. 5(23); and for the chamferred sections interrelated to the shoes bidirectional cushioning FIG. 3(34)(35).

A conventional midsole is molded of resilient foamed polyurethane type material with a lesser overall thickness for the forepart and waist than for the back part or heel, which is thicker. The top view of the heel (midsole) as shown in FIG. 4(15), depicts the heel as being the shape of a horse shoe. The perimeter of the vertical walls of the upper midsole cavity FIG. 4(30) is generally congruent with the heel of the shoe. The floor of the upper midsole cavity FIG. 3(30A) commences from a point somewhat, rearwardly and perpendicularly coinciding with the juncture FIG. 3(34) of the chamfer of the rear of the midsole (heel) and the horizontal portion continuing to the juncture FIG. 3(35) of the forward midsole (heel) chamfer.

The rear wall and the side walls of the upper midsole cavity FIG. 4(30) are inward from the rear and sides of the inner wall of the fixed lower counter FIG. 4(14) leaving clearance for a proper fit and function of the cushion assembly FIG. 3(21) and FIG. 4(21). The front wall of the upper midsole cavity FIG. 3(30) and FIG. 4(30) is a line connecting the forward ends of the upper midsole cavitys side walls at a point somewhat forwardly and perpendicularly to the junction FIG. 3(35) of the forward midsole (heel) chamfer. The depth of the upper midsole cavity is generally equal to the thickness of the cushion assembly less the length of the positioning studs FIG. 5(19).

The insole FIG. 3(18), FIG. 4(18) and the insole liner FIG. 3(18A) and FIG. 4(18A) have a hollow in their surface above the upper midsole cavity conforming to the perimeter of the vertical walls of the upper midsole cavity FIG. 4(30) which also allows for the proper fit and function of the cushion assembly FIG. 3(19)(20)(21) and FIG. 4(21).

The twelve lower midsole cavities FIG. 3(23) and FIG. 4(23) (outer rings) commence at the floor FIG. 3(30A) of the upper midsole cavity FIG. 3(30) and extend downward through the remainder of the midsole FIG. 3(23 typical). The lower twelve midsole cavities FIG. 4(23) are positioned in three files of four to provide the maximum amount of load spreading from the patient's heel through the resilient gel elliptical oblique pyramidal terraces of the upper portion of the cushion assembly then through the flexible lower portion of the cushion assembly to the calibrated cushioning springs and continue to maintain the option of the cushion assembly slanting as desired by the patient with adjustment of the calibrated springs. The wearing surface FIG. 3(17) is attached to the bottom of the midsole FIG. 3(15) creating the floor for the lower midsole cavities FIG. 3(23).

The resilient face of the heel wearing surface is the area between FIG. 3(35) and FIG. 3(34).

This face is bordered upwardly by the full depth of the midsole from the vertical walls of the upper midsole cavity FIG. 3(30) and FIG. 4(30) to the outside walls of the midsole FIG. 3(15). The area within this border is void of any material to the floor of the upper midsole cavity FIG. 5(30A). The area below this extending to the inside face of the wearing surface is further void of material within the twelve lower midsole spring cavities FIG. 3(23) and FIG. 4(23). This catacombic state of the heel of the midsole combined with the fore FIG. 3(35) and aft FIG. 3(34) chamfers of the midsole provide both flexible and resilient characteristics to the face of the heel for its contribution to the overall bidirectional uninterrupted unimpeded series of adjustable cushioning of the heel within the scope of the present invention.

The floating cavity liners FIG. 3(33), FIG. 4(33)(third inner ring) located within each of the lower spring cavities are hard thin plastic tubes with an outside diameter allowing clearance for vertical movement of the tubes within the midsole cavities and inside diameter to allow free movement of the springs. The length of the liners are generally two thirds of the depth of the lower midsole cavities. This allows bidirectional compression of the lower midsole without interference from the liners.

The springs FIG. 3(22), FIG. 4(22) and FIG. 5(22) are manufactured from steel spring wire of varying diameters and numbers of coils or partial coils then zinc plated. The springs used in the present invention are not more than one half inch in outside diameter. The length of the springs is the sum of the depth of the lower midsole spring cavities FIG. 3(23) and the depth of the upper midsole cavity FIG. 3(30). The spring ends are ground flat so they will fit flushly with the lower face of the cushion assembly and the top of the wearing surface FIG. 3(17).

A compression spring is designed to achieve its labeled resistance value at a point well before it reaches full compression. This is significant as the depth of the area surrounding the lower midsole cavities, wherein the springs are partially housed, precludes full compression of the springs which otherwise would then result in a barrier like hard surface.

It is important to interject that the patient has an option of several levels of spring compressive values which will provide the buoyant elastic cushioning or floating feeling. The lesser compressive values will result in a softer cushioned walk at the cost of walking slowly with an occasional shift into the secondary resilient elastic cushioning. As the heel pain subsides, the spring compressive values may be increased incrementally to increase the walking pace with a higher percentage of buoyantly elastic cushioning.

As stated the corrective devices for adjusting pronation are hard plastic inserts supporting the foot from the heel through the ball resulting in discomfort to the wearer and discarded for this reason.

The cushioning device within the present invention has the capability of directing contouring forces to the heel with no discomfort. If the heel requires upward adjustment on the left and the existing 12 springs are of the proper cushioning values, the left file of 4 springs FIG. 4(22) are replaced with the next higher cushioning value springs resulting in a gentle upward adjustment that can be tolerated, if noticed, during daily wear. At the appropriate time the file of the 4 left springs is replaced with the next higher cushioning value springs, this file replaces the middle file whereupon the adjustment continues with the left file receiving springs of higher cushioning values, placing the replaced left file springs in the center file cavities, and in turn placing the center file springs into the right file cavities.

This sequence can be repeated until a satisfactory adjustment is obtained and maintained for the heel. This adjustment may transcend to the arch of the foot. In any event if more forward part adjustments are required a soft pad may be placed in the arch area for soft arch support. Obviously the plane of the cushion assembly FIG. 4(21) is adjustable for any and all directions and levels of cushioning values.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An oxford shoe for diminishing vertical and horizontal heel pressure diminishment comprising:

a midsole with a cavity located in the upper surface of the midsole in the heel portion of the midsole, a plurality of voids located within the cavity, the cavity conformed to accommodate a floating laminated cushioning assembly;

the midsole is formed of resilient foamed material for cushioning;

a lower stiffened fixed counter;

an upper portion of the floating laminated cushion assembly is formed of resilient plastic with an elliptical oblique terrace at the top of the cushion followed beneath by a plurality of generally concentric terraces or partial terraces increasing in area until reaching a lower portion of the floating laminated cushion assembly and provides at its lower surface a plurality of blunt cone shaped positioning studs shaped to enter with clearance the top of the voids of the midsole;

a plurality of calibrated compression springs located in the voids of the midsole;

a plurality of floating spring liners located within each of the voids and which are hard thin plastic tubes with an outside diameter allowing clearance from the voids and an inside diameter to allow free movement of the calibrated compression springs;

an upper having a waist portion;

the lower stiffened fixed counter is attached to the midsole and meets upwardly adjacently with a supple upper floating counter which is attached to a padded floating collar;

a floating adjusting strap is attached to the lower part of the supple upper floating counter and covers a major part of the lower stiffened fixed counter, unsecured ends of the floating adjusting strap extending forwardly from the supple upper floating counter over the waist of the shoe, fastening devices attached to said unsecured ends which mate with fastening devices attached to the side of the waist which provides the means of securing and adjusting travel of the padded floating collar;

a multiplicity of spacing studs located on the side and rear of the midsole with attaching devices located within the midsole.

* * * * *